US006763829B2

(12) United States Patent
Jaffe et al.

(10) Patent No.: US 6,763,829 B2
(45) Date of Patent: Jul. 20, 2004

(54) RELIABILITY-ENHANCED APPARATUS OPERATION FOR RE-BREATHING AND METHODS OF EFFECTING SAME

(75) Inventors: Michael B. Jaffe, Cheshire, CT (US); David R. Rich, Glastonbury, CT (US); John A. Triunfo, Jr., Fairfield, CT (US); Paul B. Gunneson, Cheshire, CT (US); Eric P. Wigforss, Durham, CT (US)

(73) Assignee: NTC Technology, Inc., Wilmington, DE (US)

( * ) Notice: Subject to any disclaimer, the term of this patent is extended or adjusted under 35 U.S.C. 154(b) by 0 days.

(21) Appl. No.: 10/047,573

(22) Filed: Jan. 14, 2002

(65) Prior Publication Data

US 2002/0059933 A1 May 23, 2002

Related U.S. Application Data

(62) Division of application No. 09/410,355, filed on Sep. 30, 1999, now Pat. No. 6,575,164.
(60) Provisional application No. 60/104,347, filed on Oct. 15, 1998.

(51) Int. Cl.[7] .................................................. A62B 9/02
(52) U.S. Cl. ........................... 128/205.24; 128/204.18; 128/205.23; 251/12; 137/557
(58) Field of Search ..................... 128/200.24, 200.22, 128/203.12, 203.14, 204.18, 204.21, 204.24, 204.25–204.27, 205.12, 205.17, 205.18, 205.22, 205.24; 137/187.554, 557; 251/12–63.6

(56) References Cited

U.S. PATENT DOCUMENTS

| 4,188,946 A | | 2/1980 | Watson et al. |
| 4,281,651 A | | 8/1981 | Cox |
| 4,706,930 A | * | 11/1987 | Lexen ........................... 251/26 |
| 4,796,661 A | | 1/1989 | Hishinuma et al. |
| 4,930,501 A | | 6/1990 | Bird |
| 5,094,235 A | | 3/1992 | Westenskow et al. |
| 5,379,650 A | | 1/1995 | Kofoed et al. |
| 5,431,182 A | * | 7/1995 | Brown ........................ 137/85 |
| 5,503,145 A | | 4/1996 | Clough |
| 5,535,633 A | | 7/1996 | Kofoed et al. |
| 5,577,498 A | | 11/1996 | Yoshida et al. |
| 5,692,537 A | | 12/1997 | Arian et al. |
| 5,789,660 A | | 8/1998 | Kofoed et al. |
| 5,793,044 A | | 8/1998 | Mace et al. |
| 6,024,089 A | | 2/2000 | Wallace et al. |
| 6,042,550 A | * | 3/2000 | Haryadi et al. ............. 600/504 |
| 6,258,038 B1 | | 7/2001 | Haryadi et al. |
| 6,305,397 B1 | | 10/2001 | Ryder |
| 6,575,164 B1 | * | 6/2003 | Jaffe et al. ............. 128/205.24 |

OTHER PUBLICATIONS

Capek, J. and Roy, R., "Noninvasive Measurement of Cardiac Output Using Partial CO2 Rebreathing," *IEEE Transactions on Biomedical Engineering*, VO. 35, No. 9, Sep. 1988, pp. 653–661.
PCT Written Opinion of Feb. 28, 2001.
PCT International Search Report dated Feb. 10, 2000.

\* cited by examiner

*Primary Examiner*—Glenn K. Dawson
(74) *Attorney, Agent, or Firm*—Michael W. Haas

(57) ABSTRACT

Methods and apparatus for enhancing reliability of, and monitoring, the operation of airway valves to enhance patient safety. Pneumatic control line pressure (positive or negative) for actuation of the airway valve may be specified at a given magnitude or within a selected range and monitored continuously. Reduced or excessive pressure may be compensated by actuation of a pressure source or a bleed valve, and monitoring may be effected so as to warn the user of any deviation from the range, or deviations of selected magnitudes or frequencies or a combination thereof. The inspired volume of $CO_2$ may be monitored using air flow and $CO_2$ sensing, with detection of excessive $CO_2$ volume triggering a warning. Similarly, measured end-tidal or end-inspired $CO_2$ or other appropriate measures of $CO_2$ concentration may be employed as a warning trigger. Other driving energy sources for airway valves, and monitoring thereof, are also disclosed.

21 Claims, 3 Drawing Sheets

US 6,763,829 B2

RELIABILITY-ENHANCED APPARATUS OPERATION FOR RE-BREATHING AND METHODS OF EFFECTING SAME

This application is a divisional of application Ser. No. 09/410,355 filed Sep. 30, 1999, now U.S. Pat. No. 6,575,164, which claims the benefit of U.S. provisional patent application Serial No. 60/104,347, filed Oct. 15, 1998.

BACKGROUND OF THE INVENTION

1. Field of the Invention

The present invention relates to breathing circuits affording a re-breathing capability and, more specifically, to reliability and safety enhancements to apparatus employed to divert an exhaled breath volume for re-breathing by a patient and to subsequently remove such volume from the breathing circuit after re-breathing.

2. State of the Art

A so-called "airway" valve having a re-breathing mode and installed in a ventilator or other breathing circuit (the term "ventilator" being used generically herein to encompass various types of breathing circuits) selectively controls the diversion of an exhaled breath volume from the primary passage of the circuit into a "deadspace" volume defined by a chamber or other vessel such as a loop of hose for subsequent re-breathing by the patient. The re-breathing of the $CO_2$-laden exhaled breath volume initiates a change in respiratory $CO_2$ concentration which may be employed to estimate cardiac output in a non-invasive manner. A discussion of a partial re-breathing technique wherein an additional, fixed deadspace is intermittently and briefly introduced into the ventilator circuit is discussed in detail in Capek, J. and Roy, R., "Noninvasive Measurement of Cardiac Output Using Partial $CO_2$ Rebreathing," *IEEE TRANSACTIONS ON BIOMEDICAL ENGINEERING*, VOL. 35, NO. 9, SEPTEMBER 1988, pp. 653–661, the disclosure of which is hereby incorporated in its entirety by this reference.

An airway valve employed to divert an exhaled air volume into the deadspace volume, to subsequently add the diverted volume into the ventilator circuit for re-breathing and then to remove it from the breathing circuit requires a high degree of reliability. Specifically, failure to remove the added volume after an appropriately brief period of time results in an increased volume of inspired $CO_2$, with an attendant higher level of ventilation and arterial $CO_2$.

An exemplary breathing circuit including a deadspace volume for partial re-breathing defined by a loop of hose is schematically illustrated in FIG. 1 of the drawings. Exemplary breathing circuit 500 includes a tubular airway 502 that communicates air flow to and from the lungs of a patient. Tubular airway 502 may be placed in communication with the trachea of the patient by known intubation processes, by connection to a breathing mask positioned over the nose and/or mouth of the patient, by a mouthpiece for the patient or via an endotracheal tube. A flow meter 504, which is typically referred to as a pneumotachometer, and a carbon dioxide sensor 506, which is typically referred to as a capnometer, are disposed between tubular airway 502 and a length of hose 508, and are exposed to any air that flows through breathing circuit 500. Suitable pneumotachometers are disclosed in U.S. Pat. Nos. 5,379,650 and 5,535,633, and a suitable capnometer is disclosed in U.S. Pat. No. 5,793,044. If desired, a combined air flow and carbon dioxide sensor such as that disclosed in U.S. Pat. No. 5,789,660 may be employed in lieu of discrete flow and gas sensors. Both ends of another length or loop of tubing 510, which may be referenced as defining a deadspace or re-breathing volume 512, communicate with hose 508. Deadspace volume 512 may optionally include an expandable section 514, which may be provided by the use of corrugated tubing for tubing loop 510. A Y-piece 516, disposed on hose 508 opposite flow meter 504 and carbon dioxide sensor 506, facilitates the connection of an inspiratory hose 518 and an expiratory hose 520 to breathing circuit 500 and the flow communication of the inspiratory hose 518 and expiratory hose 520 with hose 508.

The two ends of tubing loop 510 defining deadspace volume 512 are connected to a two-mode airway valve 550, the two modes being a normal operating mode and a re-breathing mode. During normal breathing, airway valve 550 is maintained in the normal operating mode to prevent inhaled and exhaled air from flowing through deadspace volume 512. Airway valve 550 may be selectively actuated to shift from the normal operating mode to the re-breathing mode to divert a volume of a patient's exhaled breath into deadspace volume 512, the breath volume being subsequently removed from deadspace volume 512 for re-breathing by the patient. Subsequent to re-breathing, airway valve 550 is shifted back to the normal operating mode so that the re-breathed air volume is expired through hose 508 and expiratory hose 520. During inhalation, gas flows into inspiratory hose 518 from the atmosphere or a ventilator (not shown). Processing unit 522 (preferably included within a patient monitor and hereinafter referred to as a "monitor processing unit") processes air flow and carbon dioxide input signals from flow meter 504 and 506 (or preliminary processing units associated therewith as known in the art), and preferably directly or indirectly controls operation of airway valve 550 to shift same between the normal operating mode and the re-breathing mode.

Airway valves such as valve 550 illustrated in FIG. 1 may be controlled pneumatically via a control line (tubing) which actuates the valve employing an actuation energy source comprising either a positive air pressure (i.e., a pressure greater than the internal breathing circuit pressure) or a negative air pressure (i.e., a partial vacuum lower than internal breathing circuit pressure). Thus, there is always a risk of a leak, tubing disconnect, pump failure, power loss or, however unlikely, a valve component jam or failure. Accordingly, it would be desirable to provide enhanced assurance that the expired breath volume added to the circuit from the deadspace volume is removed from the circuit by appropriate switching of the airway valve, by reversion of the airway valve to a normal operating mode upon partial or total failure of the actuation energy source or delivery system, and by alerting the clinician to any problems with the actuation or control of the airway valve.

It would also be desirable to afford enhanced reliability to a variety of apparatus which may be employed to provide a deadspace volume or otherwise cause re-breathing of a patient's $CO_2$-laden exhalations.

BRIEF SUMMARY OF THE INVENTION

The present invention includes methods and apparatus for enhancing reliability of, and monitoring, the operation of various apparatus for providing a breathing circuit with a re-breathing capability. As used herein, the term "breathing circuit" includes and encompasses any apparatus through which a patient or other subject may breath, such as, without limitation, ventilator breathing circuits, masks, mouthpieces, and endotracheal tubes.

In one aspect of the invention, fluid control line pressure (positive or negative) for actuation of a pneumatic airway valve for diverting an exhalation into a tubing loop or other receptacle or element defining or providing a deadspace volume may be specified as a selected pressure or within a selected range and monitored.

In a positive pressure pneumatic system, pressure reduced below a selected threshold may be compensated by actuation of a pump or a vessel containing compressed air, while pressure elevated above a selected threshold may be compensated by a bleed valve open to the ambient environment.

In a negative pressure pneumatic system, pressure elevated above a selected threshold may be compensated by actuation of a vacuum pump or opening of a valve connected to a vacuum line, while pressure reduced below a selected threshold may be compensated by opening an inlet valve to the ambient environment.

Monitoring of control line pressure may be effected on an intermittent (periodic sampling) or continuous basis and a controller, or processor such as a patient monitor processor linked to the controller, programmed so as to warn the user of any deviation from a selected pressure, a selected pressure range, or pressure deviations of selected magnitudes or frequencies or a combination thereof.

It is also contemplated that hydraulic, electrical, magnetic, mechanical and light or other radiation sources may be employed as driving energy sources to actuate an airway valve or other apparatus for providing a deadspace and monitored in appropriate ways to provide enhanced reliability according to the invention.

Furthermore, hardware and software "watchdogs" may be incorporated into the controller for the valve or the monitor processing unit with which such controller is associated in order to preclude a software error from inadvertently causing an airway valve or other apparatus initiating re-breathing to maintain the breathing circuit in the re-breathing state.

In another aspect of the invention, the volume or level of $CO_2$ inspired by the patient may be monitored using a sensor which measures both air flow and $CO_2$, or individual air flow and $CO_2$ sensors. Detection of excessive inspired $CO_2$ volume triggers a warning. Similarly, end-tidal or end-inspired $CO_2$ concentration or other appropriate measures of $CO_2$ measured with a $CO_2$ sensor may be employed as a warning trigger.

In still another aspect of the invention, monitoring of the correct operation of an airway valve may be effected by using the patient monitor to analyze $CO_2$ or other gas waveforms (such as, for example, $O_2$ or $N_2$), either alone or optionally in combination with air pressure or flow waveforms (or both) already being processed for other purposes to ascertain whether the response expected for a particular airway valve mode (normal operating or re-breathing) is actually being produced. If the response is not as expected, an alarm or other alert may be generated to alert the operator. Thus, the system is "self-checking", in that the monitor is able to ascertain whether the airway valve actually did shift from one mode to another, responsive to the applied actuation pressure, and if a leak, blockage or mechanical failure has occurred in the airway valve actuation system or perhaps the valve itself. In this embodiment, no actual monitoring of control line pressure would be required, although it is contemplated that such monitoring in combination with waveform analysis might be effected for redundancy.

DETAILED DESCRIPTION OF THE INVENTION

Figure 1:
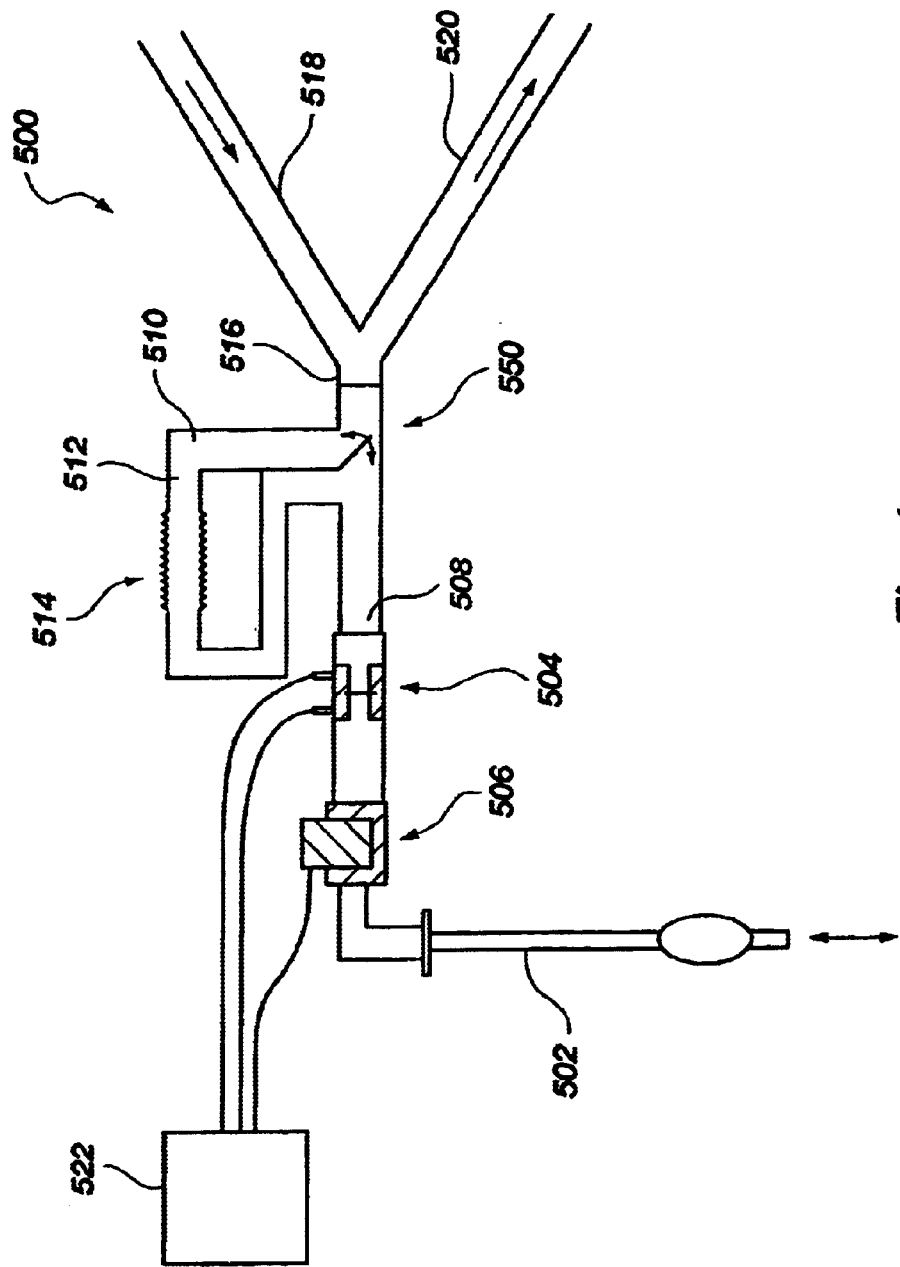
FIG. 1 is a schematic drawing of a conventional breathing circuit including a pneumatically operated re-breathing valve.
Figure 2:
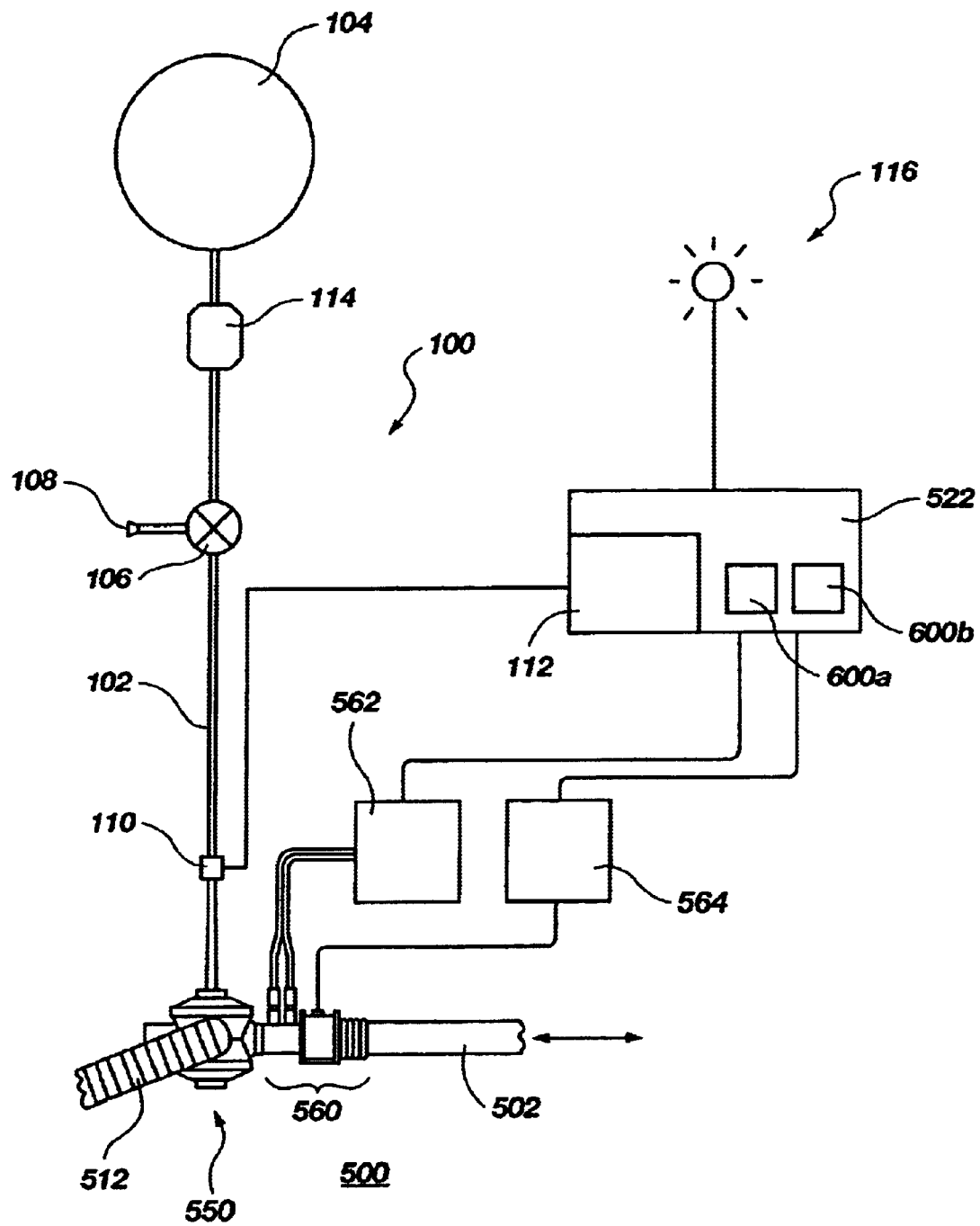
FIG. 2 is a semi-schematic drawing of breathing circuit components including a pressure-actuated airway valve for re-breathing and an associated flow and $CO_2$ sensor arrangement modified in accordance with the present invention.

Referring now to FIG. 2 of the drawings, an exemplary pneumatically actuated airway valve 550 is depicted in association with a combined air flow and $CO_2$ sensor 560, such as that described in previously referenced U.S. Pat. No. 5,789,660. One particularly preferred airway valve is disclosed in various embodiments in U.S. patent application Ser. No. 09/173,517 filed Oct. 15, 1998, assigned to the assignee of the present invention and incorporated herein by this reference. The airway valve as disclosed in the foregoing patent application is spring-biased to a normal mode, requiring application of a positive pneumatic pressure to shift to a re-breathing mode and divert an exhalation into a tubing loop. Of course, the present invention is not limited to the valve as disclosed in the foregoing patent application. Two pressure signals from the flow sensor portion of combined sensor 560 providing a differential indicative of air flow rate between airway valve 550 and the patient are detected by transducers in flow processing unit 562, which outputs a flow signal to patient monitor processing unit 522. A $CO_2$ processing unit 564 processes the output from the $CO_2$ sensor portion of combined sensor 560 and outputs a $CO_2$ concentration signal to patient monitor processing unit 522.

Airway valve 550 may be selectively actuated by valve control system 100, which comprises control line tubing 102 connected to a pressure source 104. Pressure source 104 may comprise either a positive or negative pressure source as known in the art, but preferably comprises a positive pressure source 104 such as a vessel containing compressed air or, more preferably, a pump to provide same at a suitable magnitude on demand. Such a pressure source 104 in the form of compressed air is commonly made available as needed through lines extending to a plurality of locations via pneumatic taps distributed throughout a health care installation such as a hospital or convalescent care facility. However, line pressure is usually high enough so that a regulator is required, making a pump preferable.

Pressure source 104 may feed control line tubing 102 through a valve 106, which may comprise a conventional spring-loaded, two-position solenoid vent valve normally in an open state to vent control line tubing 102 to ambient air pressure. If a pump is employed as pressure source 104, two events must occur in order to shift airway valve 550 to the re-breathing mode: first, the pump must be actuated (for example, electrically, by closure of a switch) and second, the solenoid valve 106 must be electrically actuated to create a closed system between pressure source 104 and airway valve 550. It is preferred that the solenoid valve be closed before the pump is actuated, although this is not required.

In lieu of a solenoid vent valve, control line valve 106 may comprise a three-way control line valve, as known in the art. In a first position, three-way control line valve 106 communicates pressure source 104 with control line tubing 102 to initiate a pressure increase, while in a second position, three-way control line valve 106 closes off control line tubing 102 from pressure source 104 to maintain control line pressure, and in a third position, three-way control line valve 106 communicates control line tubing 102 with a bleed orifice 108 open to a lower pressure environment and usually the ambient environment to reduce control line pressure.

In yet another alternative arrangement, two two-way control line valves may be employed at 106, one to open and close communication between pressure source 104 and control line tubing 102, the other to open and close communication between control line tubing 102 and bleed orifice 108.

With any of the foregoing arrangements, a pressure sensor 110 is placed on control line tubing 102 between a control line valve (such as 106) closest to airway valve 550 and airway valve 550 itself to monitor line pressure acting on airway valve 550. Pressure sensor 110 is electrically linked with a combined power and signal cable as known in the art to a controller 112 preferably integral with patient monitor processing unit 522, and sends substantially continuous signals thereto indicative of control line pressure in control line tubing 102. Optionally, one or more pressure-responsive switches triggered at a selected threshold pressure may be employed as a pressure sensor or sensors to provide a signal or signals, and as used herein, the term "pressure sensor" includes pressure switches. If desired, pressure sensor 110 may comprise a disposable sensor fabricated with disposable control line tubing 102 and a disposable control line valve 106 to provide single use capability, the processing circuitry for pressure sensor 110 being included within a patient monitor incorporating patient monitor processing unit 522. At least control line valve 106 (or optionally two, two-way valves arranged as described above), which may be electrically (including magnetically), pneumatically or hydraulically actuated, is also linked to controller 112. Optionally, if pressure source 104 comprises a pump associated directly with breathing circuit 500, controller 112 may be employed to actuate the pump for initiation of each re-breathing cycle or, if air pressure in a reservoir vessel associated therewith falls below a selected threshold, to cause the pump to replenish reservoir pressure.

Controller 112 preferably comprises a commercially available controller suitably programmed to respond during a re-breathing cycle, after it has closed control line solenoid vent valve 106, to open the valve 106 again to cause airway valve 550 to return to its normal operating mode. Similarly, if a three-way valve 106 is employed, controller 112 shifts control line valve 106 to its first position to elevate control line pressure and place airway valve 550 in its re-breathing mode and then to its second position to maintain control line pressure, responsive to sensed control line pressures above or below a selected threshold pressure (or below a selected lower threshold pressure and above a selected upper threshold pressure defining a pressure range, as desired) to shift control line valve 106 to either its first or third position so as to maintain control line pressure at the desired level or within the desired range. Controller 112 may be actuated responsive to a signal from patient monitor processing unit 522 to initiate a re-breathing cycle in breathing circuit 500 by switching control line valve 106 to elevate control line pressure from ambient to elevated, which may comprise pressure source pressure or something less if a suitable regulator 114 as known in the art is interposed between pressure source 104 and control line valve 106. If, in fact, a regulator 114 is employed or a pump is employed as a pressure source 104, only the above-referenced two-way solenoid vent valve need be employed to alternatively close communication between the regulated (or initiated) pressure and airway valve 550 through control line tubing 102 or to open communication between control line tubing 102 and a bleed orifice 108, which may be integral with the solenoid vent valve. In either case, responsive to the elevated control line pressure, airway valve 550 shifts to its re-breathing mode, diverting exhaled breath into deadspace 512. Similarly, a circuit re-breathing cycle may be terminated by controller 112 responsive to a signal from patient monitor processing unit 522 by switching control line valve 106 to bleed line pressure back to ambient, at which point airway valve 550 returns to its normal operating mode and the re-breathed volume is expired by the patient through expiratory hose 520. As an alternative to re-breathing cycle initiation and termination by patient monitor processing unit 522, controller 112 may itself be programmed to periodically initiate and terminate re-breathing cycles at appropriate intervals by shifting airway valve 550 between its two modes. It is also contemplated that controller 112 and patient monitor processing unit 522 may be designed and fabricated as a single, integral unit.

Alarm 116 may be incorporated into ventilator circuit 500 in association with patient monitor processing unit 522, which may be suitably programmed to actuate alarm 116 if pressure in control line valve 106 falls below or increases above a selected threshold or thresholds (when a pressure range rather than a single pressure is selected) during a re-breathing mode of airway valve 550 or increases above atmospheric pressure during a normal operating mode of airway valve 550. In the first instance, low (sub-threshold) control line pressure may signal a leak in control line tubing 102 or in its connections to control line valve 106 or airway valve 550, or a failure of pressure source 104 or in actuation of control line valve 106 to its first position. Similarly, high (supra-threshold) control line pressure may signal failure in pressure regulator 114 (if employed) or failure of control line valve 106 to operate properly when termination of a re-breathing cycle is attempted. Likewise, when control line pressure is supposed to reside at atmospheric pressure, an elevated pressure may signal failure of control line valve 106 to vent control line tubing 102 to ambient, or may signal that bleed orifice 108 is blocked or that there is a kink in the control line tubing 102. Patient monitor processing unit 522 may optionally be programmed to respond to deviations from selected threshold pressures only beyond a certain magnitude so as to avoid false alarms triggered by normal pressure sensor tolerances and transient responses initiating false readings. Similarly, patient monitor processing unit 522 may be optionally programmed to respond to repeated variations from selected pressure thresholds which are not significant enough to immediately compromise operation of airway valve 550 but which may be indicative of a pinhole leak in control line tubing 102, a leak in control line valve 106, a leak in the actuating mechanism of airway valve 550 or a loose or leaky connection between two components in the pressurized system.

Since operation of the controller 112, whether separate from or integral with patient monitor processing unit 522, is software initiated and guided, there is a possibility, however remote, that a software error occurring while airway valve 550 is in a re-breathing mode "locks up" the monitor. Without any protection from such an error, the monitor will keep airway valve 550 in the re-breathing mode, to the detriment of the patient. To avoid this situation, both the pump used as a pressure source and the solenoid vent valve have hardware "watchdogs" in the form of circuitry that requires receipt of frequent updating by the system software to function. Thus, in order to either actuate the pump or close the solenoid vent valve, the monitor must continually write to the hardware addresses which actuate these devices. Therefore, if a software or hardware error occurs and a device hardware address is no longer written to, the monitor will automatically switch to the normal operating mode.

More specifically, and in the context of the preferred embodiment, the pump used as pressure source 104 is controlled by the software. The pump control line is AC-coupled so that the software must pulse the line about every 10 milliseconds (ms) or the pump will turn off. In addition, the control line solenoid valve 106 is AC-coupled such that the software must pulse that control line about every 10 ms to keep the airway valve 550 in re-breathing mode.

Further, the software control employs two redundant time bases to keep track of the time the airway valve 550 is in re-breathing mode: a 10 ms interrupt time and a real-time clock. In addition, the software task which controls the airway valve 550 includes a watch-dog that, if not written to in the preceding 200 ms, will reset the patient monitor processing unit 522 within one (1) second.

The patient monitor processing unit 522 monitors the control line tubing 102 to make sure that the pressure in the control line tubing 102 decreases at the end of re-breathing and that the line pressure increases at the start of re-breathing. The pressure source (pump) 104 has several seconds (preferably five) to put the airway valve 550 into re-breathing mode before flagging the failure and triggering an alarm.

In addition to the foregoing watchdog system, it is desirable for enhanced reliability that two independent time sources, or clocks 600a and 600b, are employed by the patient monitor processing unit 522 to measure the re-breathing cycles or periods. Should the elapsed time signals of the two time sources 600a and 600b disagree, the airway valve 550 will be reverted back to its normal operating mode, and an alarm triggered.

It should be noted at this point that airway valve 550 may be actuated by a driving energy source other than pneumatic, for example, hydraulic, electrical, magnetic, mechanical or even light or other electromotive source. If hydraulic valve actuation is employed, pressure in the hydraulic line would be monitored. If electrical or electrically-induced magnetic actuation of airway valve 550 is employed, current or voltage (or both) in the electrical cable employed to power the airway valve 550 would be monitored. If airway valve 550 is mechanically actuated, as by a slidable wire-in-sleeve cable similar to a lawn mower throttle cable, cable position can be monitored with contact or proximity switches responsive to contact by, or proximity to, a telltale on the wire. In any instance, an alarm may be triggered if a valve of at least one parameter associated with a driving energy source is detected and continued as abnormal.

Again referring to FIG. 2 of the drawings, in addition to or in lieu of control line pressure monitoring, breathing circuit 500 and specifically patient monitor processing unit 522 may be configured and programmed to monitor the inspired volume of $CO_2$ by processing the output signals from combined flow and $CO_2$ sensor 560 to detect a failure of airway valve 550 to revert to its normal operating mode. A greater than expected inspired $CO_2$ volume would indicate that the re-breathing valve's control system has failed, or that the airway valve 550 itself has failed or jammed in the re-breathing mode, triggering alarm 116. Similarly, a threshold value of end-tidal or end-inspired $CO_2$ concentration measured using a $CO_2$ sensor or the output signal from the $CO_2$ sensor portion of combined sensor 560 may be employed as a trigger for alarm 116.

Figure 3:
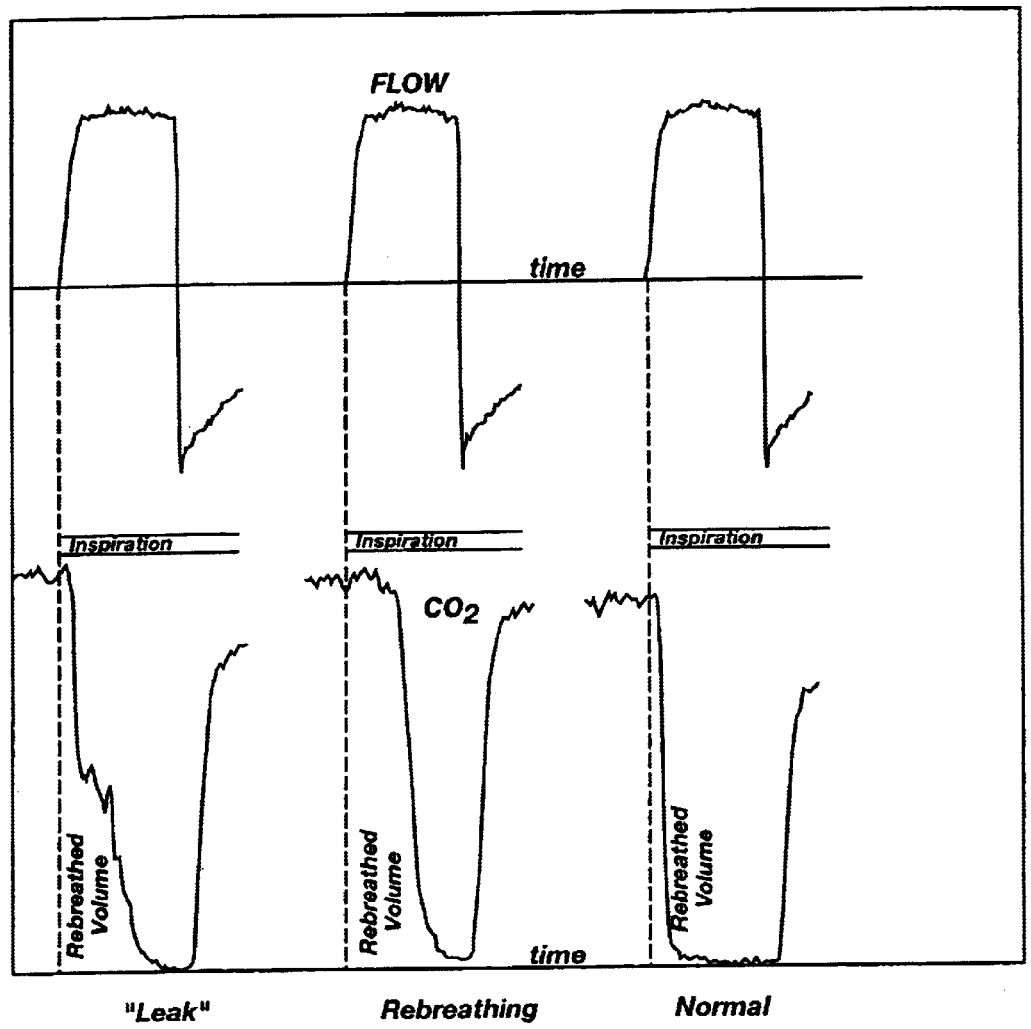
FIG. 3 is a drawing of three sets of exemplary flow and $CO_2$ waveforms during the inspiratory period and a portion of the expiratory period illustrating a leak, re-breathing and normal operation of the airway valve.

As another approach to airway valve monitoring, the flow and $CO_2$ waveforms generated responsive to the flow sensor and $CO_2$ sensor employed with the breathing circuit and conventionally employed to monitor patient condition and responses may also be employed to detect problems with operation of the airway valve 550 and its associated actuation system. Referring now to FIG. 3 of the drawings, exemplary flow and $CO_2$ waveforms are plotted one above the other against elapsed time during an exemplary inspiratory period and a portion of a subsequent expiratory period for three airway valve system conditions, "Leak", "Rebreathing" and "Normal". As can readily be seen, the flow waveforms do not vary significantly during the three conditions shown, while the Leak $CO_2$ waveform differs significantly in shape and in indicated Rebreathed Volume from either the Normal or Rebreathing waveforms. Therefore, if a valve actuation system leak has occurred when actuation pressure is applied through the control line to an airway valve to shift to the re-breathing mode, analysis of the $CO_2$ waveform by the patient monitor processing unit 522 may be used to detect a partial or complete failure of the valve to shift modes, or an initial shift followed by a return to the normal operating mode as the leak bleeds off actuation pressure. An alarm may then be initiated and additional actuation pressure automatically applied to the valve to compensate for the leak. Similarly, and by way of example only, a kink in the control line precluding application of actuation pressure to the valve will result in a Normal waveform during a time period when a Rebreathing waveform is expected. Likewise, a control line kink trapping actuation pressure at the valve after one re-breathing cycle has been initiated and completed and actuation pressure is sought to be released will result in a second Rebreathing waveform when a Normal waveform is expected. The foregoing waveform recognition technique may be generalized to smart waveform analysis of various types, so that pattern recognition, syntactic waveform analysis, neural networks, adaptive filters, etc., may be employed to determine the status of the airway valve. Waveform slope, encompassed area, peak height and/or location as well as other waveform features may be used to characterize the waveform. Since waveform analysis is already being performed for other purposes by the patient monitor processing unit, it may be readily additionally programmed to determine breathing mode as well as the existence of valve problems. "Sample" waveforms exemplary of various desirable and undesirable conditions associated with operation of the airway valve and the breathing circuit in different modes may be provided in the memory of the patient monitor processing unit for use as a reference against which to compare the actual waveforms being produced. Further, while analysis of the $CO_2$ waveform is convenient, the invention is not so limited. Instead, $O_2$, $N_2$, or any other gas which exhibits a change in concentration as a result of addition or removal of deadspace volume or $CO_2$ may be monitored for purposes of the present invention. In addition, while telltale waveform changes are emphasized in gas waveforms, flow or pressure waveforms, or both, may be employed in combination with gas waveforms.

Use of an airway valve configuration structured to return to a normal operating mode has been disclosed in co-pending U.S. patent applications Ser. No. 09/173,517, previously referenced herein, and Ser. No. 09/173,518, also filed on Oct. 15, 1998, assigned to the assignee of the present invention and the disclosure of which is also incorporated herein by reference. In each of the valves disclosed in these applications, a valve element internal to the re-breathing valve structure is spring-biased to a position occluding air flow through a re-breathing loop deadspace and directing air flow through a primary passage in the re-breathing valve to directly communicate the patient's respiration with an inspiratory hose such as hose 518 and an expiratory hose such as hose 520. The spring bias must be overcome by application of positive control line pressure in excess of that internal to the ventilator circuit plus a magnitude sufficient to overcome the spring force on the valve element. In other words, the "default" mode of operation by their design for these re-breathing valves is the normal operating mode. However, as noted above, should control line pressure be unintentionally maintained above a threshold (for example, if the valve control line becomes kinked and prevents pressure bleed-off) so as to overcome the spring force acting on the valve element when the airway valve is to be returned from its re-breathing mode to its normal operating mode, the re-breathing mode will be maintained to the possible detriment of the patient. In addition, should control line pressure be unintentionally reduced during a re-breathing cycle, a variable volume may be re-breathed, resulting in an inaccurate value being presented or a wasted re-breathing cycle. Accordingly, the present invention may provide an additional operational margin and safety factor for even these superior airway valve designs.

While the foregoing embodiments of the invention have been described in the context of "passive" devices for introducing deadspace or initiating re-breathing, an active apparatus such as a driven bellows for expanding to accept an exhalation and contracting to expel the exhalation for re-breathing by the patient are contemplated as being within the scope of the present invention. Likewise, $CO_2$ may be injected into the ventilator circuit for re-breathing, tracheal gas insufflation (TGI) may be controlled to facilitate re-breathing, transient storage of $CO_2$ may be effected by other means such as the above-mentioned bellows, a piston and cylinder arrangement or other positively-variable volume, or $CO_2$ may be chemically stored and subsequently released. In all of these instances, performance of the attempted maneuver may be monitored directly through monitoring of an actuation, drive or power source associated with the apparatus employed (e.g., pneumatic, hydraulic, electric, etc.), as well as by a detectable change in position or mode of the apparatus itself. Alternatively, or in combination with monitoring of the apparatus, the results of the attempted maneuver can be monitored in terms of proper performance by appropriate analysis of system outputs such as gas concentration, air flow, air pressure, etc., commonly taken and processed for other purposes, as described above.

While the present invention has been disclosed in terms of certain preferred embodiments, those of ordinary skill in the art will understand and appreciate that it is not so limited. Specifically and without limitation, additions, deletions and modifications to the disclosed embodiment may be effected without departing from the scope of the invention as defined by the claims. Similarly, the presence of less than all of the features of the disclosed embodiment does not remove the invention from the scope of the claims.

What is claimed is:

1. A method of enhancing reliability of operation of a pressure-actuated airway valve for a breathing circuit, the airway valve having a first mode for permitting air flow substantially directly through the airway valve and a second mode for providing a re-breathing capability to the breathing circuit, comprising:

providing a control line extending from a source of pressurized fluid to the airway valve to selectively effect a change in mode of the airway valve between the first mode and the second mode through a change in an actuation pressure provided to the airway valve via the control line;

providing a control line valve disposed in the control line between the source of pressurized fluid and the airway valve, wherein the control line valve is configured for selective communication between the control line and an ambient environment;

detecting pressure within the control line; and correcting a detected control line pressure deviation from at least one selected magnitude of control line pressure by adjusting the communication between the control line and ambient environment so as to control the actuation pressure applied to the airway valve.

2. The method of claim 1, further comprising detecting control line pressure when the airway valve is in the first mode and in the second mode, correcting detected control line pressure deviation from a first selected magnitude of control line pressure when the airway valve is in the first mode and correcting detected control line air pressure deviation from a second selected magnitude of control line pressure when the airway valve is in the second mode.

3. The method of claim 2, wherein each of the first and second selected magnitudes of control line pressure comprises a range of magnitudes.

4. The method of claim 1, wherein correcting the detected control line pressure deviation includes selectively controlling communication between the source of pressurized fluid and the airway valve through the control line.

5. The method of claim 1, wherein correcting the detected control line pressure deviation includes maintaining the control line pressure above a selected magnitude by actuating the control line valve.

6. The method of claim 1, wherein correcting the detected control line pressure deviation includes maintaining the control line pressure below a selected magnitude by actuating the control line valve.

7. The method of claim 1, wherein correcting the detected control line pressure deviation includes maintaining the control line pressure within a selected range of magnitude.

8. The method of claim 1, further comprising shifting the airway valve between the first and the second modes by actuation of the control line valve.

9. The method of claim 8, further comprising monitoring a condition of a patient and wherein the shifting of the airway valve by the control line valve is done based on the monitored condition of the pateint.

10. The method of claim 8, wherein the shifting step is done periodically.

11. The method of claim 10, wherein correcting the detected control line pressure deviation includes maintaining the control line pressure above a selected magnitude by actuating the control line valve.

12. The method of claim 10, wherein correcting the detected control line pressure deviation includes maintaining the control line pressure below a selected magnitude by actuating the control line valve.

13. The method of claim 10, wherein correcting the detected control line pressure deviation includes maintaining the control line pressure within a selected range of magnitudes.

14. The method of claim 1, further comprising actuating an alarm responsive to the actuation pressure being above a selected magnitude.

15. The method of claim 1, further comprising actuating an alarm responsive to the actuation pressure being below a selected magnitude.

16. The method of claim 1, further comprising actuating an alarm responsive to the actuation pressure being outside of a selected range of magnitudes.

17. The method of claim 1, further comprising actuating an alarm responsive to the actuation pressure being above a first selected magnitude when the airway valve is in the first mode and responsive to the actuation pressure being below a second selected magnitude when the airway valve is in the second mode.

18. The method of claim 1, further comprising actuating an alarm responsive to an occurrence of a selected number of deviations of the actuation pressure from a selected pressure magnitude.

19. The method of claim 18, wherein the alarm is actuated responsive to the occurrence of the selected number of deviations if each of such deviation is of at least a selected magnitude with respect to the selected pressure magnitude.

20. The method of claim 1, further comprising computing inspired $CO_2$ volume based an output of an air flow sensor and a $CO_2$ sensor, and triggering an alarm responsive to a deviation of the computed inspired $CO_2$ volume from a selected magnitude or range of magnitudes.

21. The method of claim 1, further comprising computing at least one of end-tidal or end-inspired $CO_2$ concentration responsive to signals from a $CO_2$ sensor located to detect $CO_2$ in the breathing circuit between the airway valve and a patient, and triggering an alarm responsive to a deviation of at least one computed $CO_2$ concentration from a selected magnitude or range of magnitudes.

* * * * *